US008747885B2

(12) United States Patent
Ishima et al.

(10) Patent No.: US 8,747,885 B2
(45) Date of Patent: Jun. 10, 2014

(54) EXTERNAL PATCHES CONTAINING ETOFENAMATE

(75) Inventors: Tomohiro Ishima, Higashikagawa (JP); Hiroyuki Yamasaki, Higashikagawa (JP); Masahiro Yamaji, Higashikagawa (JP)

(73) Assignees: Teikoku Seiyaku Co., Ltd., Kagawa (JP); Drossapharm AG, Basel (CH)

( * ) Notice: Subject to any disclaimer, the term of this patent is extended or adjusted under 35 U.S.C. 154(b) by 62 days.

(21) Appl. No.: 11/793,231

(22) PCT Filed: Dec. 15, 2004

(86) PCT No.: PCT/JP2004/019143
§ 371 (c)(1),
(2), (4) Date: Jun. 15, 2007

(87) PCT Pub. No.: WO2006/064576
PCT Pub. Date: Jun. 22, 2006

(65) Prior Publication Data
US 2008/0089926 A1    Apr. 17, 2008

(51) Int. Cl.
*A61K 9/70*    (2006.01)
*A61M 35/00*    (2006.01)

(52) U.S. Cl.
USPC ........... 424/443; 424/447; 424/448; 424/449; 514/535; 514/536

(58) Field of Classification Search
None
See application file for complete search history.

(56) References Cited

U.S. PATENT DOCUMENTS

| | | | |
|---|---|---|---|
| 4,455,146 A * | 6/1984 | Noda et al. | 424/448 |
| 4,623,346 A | 11/1986 | von Bittera et al. | |
| 4,661,104 A | 4/1987 | von Bittera et al. | |
| 4,738,670 A | 4/1988 | von Bittera | |
| 4,963,361 A * | 10/1990 | Kawazi | 424/443 |
| 5,208,035 A * | 5/1993 | Okuyama et al. | 424/446 |
| 5,464,628 A | 11/1995 | Jalonen et al. | |
| 6,620,430 B2 * | 9/2003 | Takada et al. | 424/449 |
| 6,703,043 B1 | 3/2004 | Himmelsbach et al. | |
| 2003/0100852 A1 * | 5/2003 | Kawaji | 602/8 |
| 2005/0019382 A1 | 1/2005 | Kummer et al. | |
| 2009/0274747 A1 * | 11/2009 | Yasukochi et al. | 424/448 |

FOREIGN PATENT DOCUMENTS

| | | |
|---|---|---|
| EP | 0 285 181 | 10/1988 |
| JP | 58-67617 | 4/1983 |

(Continued)

OTHER PUBLICATIONS

Machine translation of JP-A-1997-291028, pp. 1-6.*

(Continued)

*Primary Examiner* — Suzanne Ziska
*Assistant Examiner* — Ivan Greene
(74) *Attorney, Agent, or Firm* — Wenderoth, Lind & Ponack, L.L.P.

(57) ABSTRACT

The present invention provides to patches having excellent skin-permeability and therapeutic effect by the drug with lower irritation. In an external patch in which an adhesive layer containing an adhesive base and a drug are laminated with a backing, the external patch wherein the adhesive base contains 5-50% by weight of synthetic rubber polymer, 10-60% by weight of adhesive resin and 25-60% by weight of liquid paraffin, and the drug is etofenamate. According to the present invention, there is obtainable the patches having excellent skin-permeability and therapeutic effect by the drug with lower irritation.

1 Claim, 1 Drawing Sheet

(56) References Cited

FOREIGN PATENT DOCUMENTS

| JP | 7-215850 | | 8/1995 |
|---|---|---|---|
| JP | 9-291028 | | 11/1997 |
| JP | A-1997-291028 | * | 11/1997 |
| JP | 10-45569 | | 2/1998 |
| WO | A-1997-219028 | * | 11/1997 |
| WO | WO 02/09653 | * | 2/2002 |
| WO | WO 0209653 A1 | * | 2/2002 |

OTHER PUBLICATIONS

Sink, Patrick J.; "Martin's Physical Pharmacy and Pharmaceutical Sciences", 2005, Lippincott, Williams & Wilkins, pp. 231-265.*

Ansel, Howard C. et al.; "Pharmaceutical Dosage Forms and Drug Delivery Systems", 1998, Lippincott, Williams & Wilkins, pp. 296-299.*

Sweetman, Sean C.; "Martindale: The complete drug reference", Pharmaceutical Press, 2002, pp. 1-90.*

O'Neil, Maryadele J.; Heckelman, Patricia E.; Koch, Cherie B.; Roman, Kristin J.; Kenny Catherine, M.; D'Arecca, Maryann R. editors; "The Merck Index: An Encyclopedia of Chemicals, Drugs, and Biologicals," 2006; Merck & Co., Inc.; entry for "etofenamate," p. 1.*

English Language Translation of Japanese Language Patent Document JP-A-1997-291028 (Naoko Nishida et al.); Obtained from the McElroy Tranlation Company, Oct. 2011, pp. 1-18.*

Corekill, Katherine; "Skin Penetration Enhancers—Friend or Foe," retrieved from on Feb. 22, 2013, pp. 1-5.*

International Preliminary Report on Patentability for PCT/JP2004/019143.

Korean Office Action issued Apr. 30, 2012 in corresponding Korean Application No. 2007-7015789.

* cited by examiner

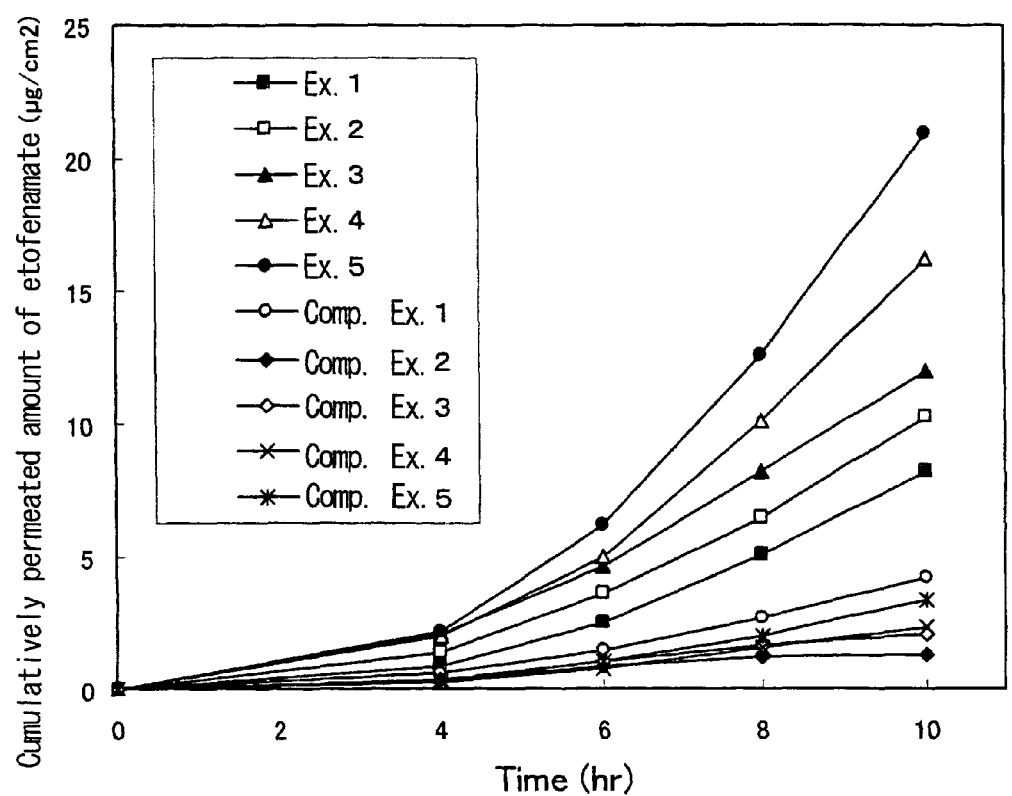

EXTERNAL PATCHES CONTAINING ETOFENAMATE

TECHNICAL FIELD

The present invention relates to an external patch in which an adhesive layer containing the adhesive base and the drug are laminated with a backing.

BACKGROUND ART

Etofenamate, a non-steroidal anti-inflammatoric analgesic, is used as a therapeutic agent for pains caused by stiff shoulders and muscle weariness, contusion, distortion and so on in form of ointments and gels. However, in regard to the ointments and the gels, the control of the amount to be administered is difficult, and as a volatile alcohol is mixed in the preparations, skin-irritation and peculiar smell thereby have been become problematic. Furthermore, when using the preparations, there is such a demerit that hands or clothes are apt to dirty.

To make up for such demerits of the preparations, there is a report on patches in which a synthetic rubber is used. For example, in Japanese patent publication A 63-246327, are described patches which contain etofenamate as a drug, styrene-isoprene-styrene block copolymer (SIS block copolymer), an adhesive resin, liquid paraffin, liquid gum and an antioxidant. However there is a room to improve the dermal permeability of etofenamate and skin-irritation in the patches.

DISCLOSURE OF INVENTION

The object of the present invention is to provide an external patch which is excellent in skin-permeability of etofenamate, has excellent anti-inflammatory activity and that is very low in skin-irritation.

BRIEF DESCRIPTION OF DRAWINGS

FIG. 1 shows the amounts of cumulatively permeated etofenamate in various patches.

SUMMARY OF THE INVENTION

The present inventors have been earnestly studied in order to resolve the above disadvantages, and as a result, have found that the patches to meet the object can be prepared by adding etofenamate to the adhesive base containing 5-50% by weight of a synthetic rubber, 10-60% by weight of an adhesive resin and 25-60% by weight of liquid paraffin.

Namely the present invention relates to in an external patch in which an adhesive layer containing the adhesive base and the drug are laminated with a backing, the external patch wherein the adhesive base contains 5-50% by weight of a synthetic rubber, 10-60% by weight of an adhesive resin and 25-60% by weight of liquid paraffin, and the drug is etofenamate.

MODE FOR CARRYING OUT THE INVENTION

The synthetic rubber used in dermally absorbable patches of the present invention includes styrene-isoprene-styrene block copolymer (SIS block copolymer), polyisobutylene, isoprene rubber, styrene-butadiene-styrene block copolymer, silicon rubber, etc. The synthetic rubber may be used in a combination with them, but SIS block copolymer is most preferable in consideration of skin-permeability of the drug and physical property of the preparation.

The amount of the synthetic rubber is usually 5-50% by weight, preferably 5-40% by weight, and more preferably 10-25% by weight. When being less than 5% by weight, the base is not aggregated and there is a possibility that a part of the adhesive agent remains on skin when the preparation is released from skin. When being over 50% by weight, the aggregation power becomes too strong and the decrease of adhesivity occurs. Therefore, it becomes difficult to carried out the spreading step of the base due to the high viscosity of the adhesive agent in the preparing the preparation.

The adhesive resin is usually to provide the patch adhesivity to skin, and rosin resin and its derivative (rosin, rosin ester, hydrogenated rosin, hydrogenated rosin esters), petroleum resin (alicyclic hydrocarbon resin, aliphatic hydrocarbon resin), terpene resin, etc, are used as the adhesive resin. In the present invention, preferably petroleum resin, especially preferably, alicyclic saturated hydrocarbon are used from the viewpoint of dermal absorbability and skin-adhesivity.

The amount of the adhesive resin is 10-60% by weight, preferably 15-50% by weight, and more preferably 20-40% by weight. When being less than 10% by weight, the adhesivity of the patch extremely decreases. When being beyond 60% by weight, the adhesivity becomes too strong and therefore, when releasing the patch from skin, the physical stimulation occurs and the viscosity of the adhesive agent becomes too high.

The liquid paraffin have the property to make soft the adhesive agent and to improve the stickiness to skin in application and as well, to control the adhesivity to skin and to reduce the physical irritation to skin.

The amount of the liquid paraffin has very important role in the preparations of the present invention.

The amount of the liquid paraffin is 25-60% by weight, preferably 25-50% by weight, and more preferably 30-40% by weight. When being less than 25% by weight, the adhesivity becomes too strong, and when releasing the patch from skin, the physical irritation occurs. Furthermore, skin-permeability of the drug extremely reduces (see FIG. 1). When being beyond 60% by weight, the sufficient adhesivity is not attained and the aggregation power of the adhesive agent reduces. Therefore, there is a possibility to remain a part of the adhesive agent to skin.

It was also found that in the preparation of the present invention, by further adding a plasticizer to the adhesive base, skin-permeability of the drug can be enhanced.

The plasticizer used in the present invention includes triacetin, crotamiton, fatty acid esters such as diethyl sebacate, triethyl citrate, isopropyl myristate, etc., N-methylpyrrolidone, etc.

The amount of the plasticizer is usually 0.5-20% by weight, preferably 1-10% by weight, and more preferably 3-7% by weight. The plasticizer may be used in a combination of them. A combination of crotamiton and isopropyl myristate is especially preferable as the plasticizer used in the present invention.

The amount of crotamiton is preferably 0.5-5% by weight. When being less than 0.5% by weight, the effect of it is lessen. When being beyond 5% by weight, the destruction of the aggregation of the adhesive agent occurs and a part of the adhesive agent remains on skin when releasing the patch from skin. The amount of isopropyl myristate is preferably 0.5-15% by weight. When being less than 0.5% by weight, the effect of it is lessen. When being beyond 15% by weight, the destruction of the aggregation of adhesive agent occurs and a part of the adhesive agent remains on skin when releasing it from skin. The ratio of crotamiton and isopropyl myristate is preferably 1:1-1:3 when used in their combination.

The amount of etofenamate used in the present invention is usually 1-10% by weight, preferably 2-8% by weight, and more preferably 3-6% by weight. When being less than 1% by weight, the amount of the drug released is lessen, there is a high possibility not to attain the desired therapeutic effect, and when being beyond 10% by weight, it becomes difficult to prepare the preparation in relation to the other ingredients.

The patches of the present invention may contains, if necessary, other ingredients, which are usually used in the patches, such as antioxidants, fillers, preservatives, softeners, etc.

The antioxidant includes dibutyl hydroxytoluene, its derivative, tocopherol, its derivative, ascorbic acid, its derivative, etc. The filler includes calcium carbonate, magnesium carbonate, magnesium sulfate, zinc oxide, titanium oxide, silicic acid and its salt (silicon dioxide, aluminum silicate, magnesium silicate, light silicic anhydride, etc.), etc. The preservative includes parabens (p-hydoxybenzoates), etc. The softener includes petroleum oils (paraffin oil, aromatic oil, etc.), silicon oil, liquid rubbers (polybutene, liquid isoprene rubber, etc.), high molecular weight fatty acids, high molecular weight fatty acid esters, polyhydric alcohols (polyethylene glycol, propylene glycol, diethylene glycol, cyclopropylene glycol, glycerin, glycol salicylate, etc.), vegetable oils (olive oil, eucalyptus oil), etc.

The thickness of the adhesive layer of the patches of the present invention is not limited and is preferably 20-500 μm, and more preferably 70-300 μm as when being too thin the adhesivity reduces and when being too thick, the patches are readily released by rubbing with clothes.

The backing to be used in the present invention is preferably in being rich in flexibility, and includes, many kinds of woven textile, unwoven textile, a vinyl chloride film, a polyethylene film, a polyurethane film, etc. or a complexed film laminated these films.

The release liner to be used in the present invention includes films, such as polyethylene terephthalate (PET), polypropylene, polyethylene chloride, etc., and these films may be, if necessary treated by silicon to have them suitable releasability.

The patches of the present invention are prepared as follows.

Namely a synthetic rubber, an adhesive resin, liquid paraffin, a softener, an antioxidant, a filler, etc. were dissolved under heating. After cooled, etofenamate, and if necessary a plasticizer, are added thereto and the mixture is kneaded under stirring. Thus obtained base is spread on a silicon-treated PET film, laminated with a backing (polyester textile) and cutting a desired size to prepare the dermally absorbable patches of the present invention.

The present invention is more concretely explained by the following examples, but the present invention is not limited by them.

The term "part" in the examples means "part by weight", if it is not defined otherwise.

According to the method mentioned above, dermally absorbable patches having ingredients shown in Example 1 to Example 5 were prepared.

A preparation (patch) containing ingredients of Example 5 except liquid paraffin (5 parts) instead of etofenamate (5.0 parts) was also prepared as a control preparation.

Example 1

| | |
|---|---|
| Etofenamate | 5.0 (parts) |
| SIS block copolymer | 15.0 |
| Hydrogenated rosin glycerin ester | 30.0 |

-continued

| | |
|---|---|
| Liquid paraffin | 38.0 |
| Polybutene | 10.0 |
| Dibutyl hydroxytoluene | 1.0 |
| Light silicic anhydride | 1.0 |
| Total | 100.0 |

Example 2

| | |
|---|---|
| Etofenamate | 5.0 (parts) |
| SIS block copolymer | 15.0 |
| Alicyclic saturated hydrocarbon | 30.0 |
| Liquid paraffin | 38.0 |
| Polybutene | 10.0 |
| Dibutyl hydroxytoluene | 1.0 |
| Light silicic anhydride | 1.0 |
| Total | 100.0 |

Example 3

| | |
|---|---|
| Etofenamate | 5.0 (parts) |
| SIS block copolymer | 15.0 |
| Alicyclic saturated hydrocarbon | 30.0 |
| Liquid paraffin | 33.0 |
| Polybutene | 10.0 |
| Isopropyl myristate | 5.0 |
| Dibutyl hydroxytoluene | 1.0 |
| Light silicic anhydride | 1.0 |
| Total | 100.0 |

Example 4

| | |
|---|---|
| Etofenamate | 5.0 (parts) |
| SIS block copolymer | 15.0 |
| Alicyclic saturated hydrocarbon | 30.0 |
| Liquid paraffin | 36.0 |
| Polybutene | 10.0 |
| Crotamiton | 2.0 |
| Dibutyl hydroxytoluene | 1.0 |
| Light silicic anhydride | 1.0 |
| Total | 100.0 |

Example 5

| | |
|---|---|
| Etofenamate | 5.0 (parts) |
| SIS block copolymer | 15.0 |
| Alicyclic saturated hydrocarbon | 30.0 |
| Liquid paraffin | 31.0 |
| Polybutene | 10.0 |
| Isopropyl myristate | 5.0 |
| Crotamiton | 2.0 |
| Dibutyl hydroxytoluene | 1.0 |
| Light silicic anhydride | 1.0 |
| Total | 100.0 |

A mixture of SIS block copolymer, hydrogenated terpene resin, liquid paraffin, polybutene and an anti-oxidant was stirred under heating. After cooled, etofenamate was added thereto and the mixture was kneaded under stirring. Thus obtained base was spread on a silicon-treated PET film, laminated with a backing (polyester textile) and cutting a desired size to prepare a patch containing ingredients of the Comparative example 1.

Comparative example 1*

| Etofenamate | 10.0 (parts) |
|---|---|
| SIS block copolymer | 30.0 |
| Hydrogenated terpene resin | 45.0 |
| Liquid paraffin | 4.5 |
| Polybutene | 10.0 |
| Anti-oxidant | 0.5 |
| Total | 100.0 |

*Example 2 of Japanese patent publication A 63-24632

Etofenamate was added to acrylic polymer and thereto was added a suitable amount of ethyl acetate in order to control the viscosity on spreading to prepare an acrilic adhesive liquid. The acrylic adhesive liquid was spread on a PET film, and the solvent was removed on drying to prepare an adhesive layer. The layer was laminated with a backing prepared by laminating a PET unwoven textile and a PET film to prepare a patch containing ingredients of Comparative example 2.

Comparative Example 2

| Etofenamate | 5.0 (parts) |
|---|---|
| Acrylic adhesive agent | 95.0 |
| Total | 100.0 |

Etofenamate and isopropyl myristate were added to acrilic polymer, and the mixture was dealt in accordance with the method of Comparative example 2 to prepare a patch containing ingredients of Comparative example 3.

Comparative Example 3

| Etofenamate | 5.0 (parts) |
|---|---|
| Acrylic adhesive agent | 90.0 |
| Isopropyl myristate | 5.0 |
| Total | 100.0 |

Etofenamate and crotamiton were added to acrilic polymer, and the mixture was dealt in accordance with the method of Comparative example 2 to prepare a patch containing ingredients of Comparative example 4.

Comparative Example 4

| Etofenamate | 5.0 (parts) |
|---|---|
| Acrylic adhesive agent | 93.0 |
| Crotamiton | 2.0 |
| Total | 100.0 |

Etofenamate, isopropyl myristate and crotamiton were added to acrilic polymer, and the mixture was dealt in accordance with the method of Comparative example 2 to prepare a patch containing ingredients of Comparative example 5.

Comparative Example 5

| Etofenamate | 5.0 (parts) |
|---|---|
| Acrylic adhesive agent | 88.0 |
| Isopropyl myristate | 5.0 |
| Crotamiton | 2.0 |
| Total | 100.0 |

Test 1: Skin-Permeability Test in Vitro

In order to investigate skin-permeability of etofenamate, skin-permeability test in vitro (rat) was carried out by using the preparations of Examples 1, 2, 3, 4 and 5 and Comparative examples 1, 2, 3, 4 and 5. After removal of hairs of the abdomen of rats, the skin of the abdomen was taken out and fixed in a Frantz diffusion cell. In the inner part of the cell, phosphate buffered physiological saline was filled as a receptor solution. Water of 37° C. was cyclized in a jacket over the cell. Each patch was punched in a circle having diameter 2.5 cm and each circle was applied on the skin on the cell. The sampling from the receptor solution was carried out from time to time and the amount of etofenamate permeated through the skin was measured by liquid chromatography.

The result was shown in FIG. 1. According to the result, the preparation containing synthetic rubber was superior to the preparation containing acrilic adhesive agent in skin-permeability of etofenamate. In addition by making synthetic rubber contain the amount in more than 25% of liquid paraffin, skin-permeability of etofenamate was raised, and by adding crotamiton and isopropyl myristate thereto, skin-permeability was further raised.

Test 2: Inhibition Test on Edema Induced on Plantar of Limb by Carrageenin

Each patch of Examples 2 to 5, Comparative examples 1 and 2 was cut in a size of 3 cm×4 cm and the cut patch was applied on a plantar of a right hind limb of a rat on 4 hours before administration of carrageenin. One percent Carrageenin physiological saline (0.1 mL) was subcutaneously administered to the plantar of the right hind limb of the rat in order to induce edema on that region. Before administration and 4 hours later after administration, the volume of the limb was measured.

The inhibition rate of edema was calculated according to the following calculation formula:
Formula:

Rate of edema (%)={(volume of limb at 4 hours later after induction of edema (mL)−volume of limb before induction of edema (mL))/volume of limb before induction of edema (mL)}×100

Inhibition rate (%)={1−rate of edema of test sample (%)/rate of untreated control group (%)}×100

The result was shown in Table-1. All the preparations of the present invention (Examples 2 to 5) showed the inhibition of edema, especially the preparation containing crotamiton and isopropyl myristate showed statistically significant difference comparing with the control preparation in the inhibition of edema (Student's t-test $p<0.01$).

TABLE 1

| Sample | Rate of edema (%) | Rate of inhibition (%) |
| --- | --- | --- |
| Untreated | 59.0 ± 2.4 | — |
| Control | 58.9 ± 3.7 | 0.17 |
| Example 2 | 48.1 ± 2.9 | 18.5 |
| Example 3 | 42.0 ± 3.8 | 28.8 |
| Example 4 | 35.8 ± 2.0 | 39.3 |
| Example 5 | 26.5 ± 1.7 | 55.1 |
| Comparative example 1 | 52.4 ± 4.5 | 11.2 |
| Comparative example 2 | 54.6 ± 3.3 | 7.46 |

Test 3: Adhesive Test

In accordance with JIS Z0237 14: slant ball-tack method, each preparation was measured on its adhesive power. Each patch of Example 1, Example 2, Example 5, Comparative example 1, Comparative example 2 and Comparative example 5 was cut in a size of 10 cm×5 cm. The slant angle of the apparatus was set at 30° C. and the slant plate made of acrilic polymer was used, and the length of the run way and the measured part was 10 cm. The measurement was three times per each preparation and the maximum number among the number of balls which stayed for more than 5 minutes at the measured part was counted.

The result was shown in Table-2. The preparation containing synthetic rubber was superior to the preparation containing acrilic adhesive agent in adhesive power, and the adhesive power of the preparation containing further liquid paraffin (more than 25%) was improved.

TABLE 2

| Sample | Adhesive power |
| --- | --- |
| Example 1 | 22 |
| Example 2 | 22 |
| Example 5 | 24 |
| Comparative example 1 | 18 |
| Comparative example 2 | 16 |
| Comparative example 5 | 16 |

Test 4: Primary Skin-Irritation Test on Rabbit

This test was carried out using Japanese white female rabbits (8 rabbits). After removal of hairs of the back of a rabbit, each two patches were applied to right and left sides, respectively. The right side was healthy part and the left side was injured part. The injured part was injured in the shape of # by a needle for injection. Each patch of Control, Example 2, Example 5, Comparative example 1, Comparative example 2 and Comparative example 5 (n=6) was punched in a circle of a diameter having 2.5 cm and each of them was applied to the objected regions. Each applied part was fixed by a tape (band-aid, trade name). The rabbits were further wore with a protecting clothe to prevent the move of the patches applied. Twenty four hours later after application, each patch was removed, and the skin-reaction was observed on 1 hour, 24 hours and 48 hours.

The judgment was conducted in accordance of the judgment standard of Draize described in Table-3. Based on the judgment at 1 hour and 48 hours after removal of patches, the index of primary skin-irritation (P. I. I) was calculated.

The result was shown in Table-4. The preparations of the present invention used in this test were lower in the irritation.

TABLE 3

| Standard of judgment of Draize Item of observation and degree | | |
| --- | --- | --- |
| Erythema and scab | No erythema | 0 |
| | Slight erythema (barely distinctive) | 1 |
| | Clear erythema | 2 |
| | Middle to strong erythema | 3 |
| | Strong erythema with slight scab (deeply injured) | 4 |
| Edema | No edema | 0 |
| | Slight edema (barely distinctive) | 1 |
| | Slight edema (outline of swelling being clear) | 2 |
| | Middle ranked edema (swelling being to about 1 mm height) | 3 |
| | Heavily ranked edema (swelling being to more than 1 mm height and being enlarged to outside of region applied) | 4 |

TABLE 4

| | | Average score of irritation reaction (n = 6) | | |
| --- | --- | --- | --- | --- |
| Sample | State of skin | After 1 hour | After 48 hours | P.I.I. |
| Control | Normal | 0.3 | 0 | 0.3 |
| | Injured | 0.7 | 0 | |
| Example 2 | Normal | 0.5 | 0 | 0.4 |
| | Injured | 0.8 | 0.3 | |
| Example 5 | Normal | 0.2 | 0 | 0.2 |
| | Injured | 0.5 | 0 | |
| Comparative example 1 | Normal | 1.2 | 0.7 | 1.0 |
| | Injured | 1.3 | 1.0 | |
| Comparative example 2 | Normal | 1.5 | 0.5 | 1.3 |
| | Injured | 2.0 | 0.5 | |
| Comparative example 5 | Normal | 1.3 | 1 | 1.2 |
| | Injured | 1.3 | 0.7 | |

It was confirmed by the above tests that the dermally absorbable external patches containing etofenamate as an active ingredient of the present invention have excellent skin-permeability and excellent therapeutic effect by etofenamate and as well, have a higher safety and lower irritation.

The invention claimed is:

1. An external patch in which an adhesive layer consisting of an adhesive base and a drug is laminated with a backing,
wherein the adhesive base consists of 15.0% by weight of styrene-isoprene-styrene block copolymer, 30.0% by weight of alicyclic saturated hydrocarbon, 31.0% by weight of liquid paraffin, 10.0% by weight of polybutene, 5.0% by weight of isopropyl myristate, 2.0% by weight of crotamiton, 1.0% by weight of dibutyl hydroxytoluene and 1.0% by weight of light silicic anhydride,
and wherein the drug is 5.0% by weight of etofenamate.

* * * * *